(12) United States Patent
Hansel

(10) Patent No.: US 8,846,967 B2
(45) Date of Patent: Sep. 30, 2014

(54) PROCESS FOR PREPARING ALKYL PHOSPHATES

(75) Inventor: Jan-Gerd Hansel, Bergisch Gladbach (DE)

(73) Assignee: LANXESS Deutschland GmbH, Cologne (DE)

( * ) Notice: Subject to any disclaimer, the term of this patent is extended or adjusted under 35 U.S.C. 154(b) by 169 days.

(21) Appl. No.: 13/349,972

(22) Filed: Jan. 13, 2012

(65) Prior Publication Data

US 2012/0184766 A1     Jul. 19, 2012

(30) Foreign Application Priority Data

Jan. 17, 2011   (EP) ..................................... 11151165

(51) Int. Cl.
*C07F 9/09*      (2006.01)
*C07F 9/14*      (2006.01)

(52) U.S. Cl.
CPC . *C07F 9/14* (2013.01); *C07F 9/093* (2013.01); *C07F 9/091* (2013.01)
USPC ....................................................... 558/132

(58) Field of Classification Search
USPC ................................................... 558/132, 99
See application file for complete search history.

(56) References Cited

U.S. PATENT DOCUMENTS

| | | | |
|---|---|---|---|
| 2,782,128 A | 2/1957 | Paist et al. | |
| 4,056,480 A | 11/1977 | Herber | |

OTHER PUBLICATIONS

European Search Report dated Mar. 10, 2011 for EP11151165.
Oliver et al., "Diphosphate Ester Plasticizers", Ind. Eng. Chem. (1950), 42(3):488-491.

*Primary Examiner* — Kristin Vajda
(74) *Attorney, Agent, or Firm* — Jennifer R. Seng

(57) ABSTRACT

The present invention relates to a process for preparing tetraalkyl bisphosphates by reacting tetrachlorobisphosphates with alcohols, neutralizing the resultant hydrogen chloride with a base, and isolating the desired product from the reaction mixture by extraction.

19 Claims, No Drawings

PROCESS FOR PREPARING ALKYL PHOSPHATES

The present invention relates to a process for preparing tetraalkyl bisphosphates by reacting tetrachlorobisphosphates with alcohols, neutralizing the resultant hydrogen chloride with a base, and isolating the desired product from the reaction mixture by extraction.

Tetraalkyl bisphosphates are viscous liquids of low volatility and have been used for a long time for industrial applications, for example as polymer additives (see U.S. Pat. No. 2,782,128) or as hydraulic oils (see U.S. Pat. No. 4,056,480). For these applications it is typically necessary for the tetraalkyl bisphosphates to contain as few impurities as possible. Accordingly, the amount of acidic impurities, as may be determined, for example, by measuring the acid number, ought to be extremely low, since acid can lead to accelerated decomposition or corrosion. Tetraalkyl bisphosphates with an acid number of greater than about 1.0 mg KOH/g are unusable for the cited applications. Similarly to acids, impurities with bases are unwanted as well, since in the application they may act unwantedly as catalysts. Moreover, the presence of electrolytes is undesirable, since it may likewise cause corrosion problems or may lead to an incompatibility between tetraalkyl bisphosphate and a polymer matrix. Levels of metal ions of greater than about 5000 ppm, as may be determined by means of known chromatographic or spectroscopic methods, are undesirable.

Various processes for preparing tetraalkyl bisphosphates are known. However, they have deficiencies, in that the prevention or removal of the aforementioned impurities is costly and inconvenient, and so are unsuitable for industrial production. Furthermore, the known processes afford unsatisfactory yields, hence necessitating a technically costly and inconvenient removal and disposal of unused raw materials or of by-products.

U.S. Pat. No. 2,782,128 describes a process for preparing tetraalkyl bisphosphates by reaction of dialkyl chlorophosphates with diols in the presence of pyridine. The dialkyl chlorophosphate intermediate prepared in the first stage of the synthesis sequence from phosphorus trichloride, alcohol and chlorine has to be worked up with the benzene solvent and then distilled under reduced pressure. In the second stage, the by-product pyridine hydrochloride has to be precipitated by addition of diethyl ether solvent. Furthermore, residues of the pyridine have to be extracted using hydrochloric acid, and the product phase then has to be washed again with sodium hydroxide solution until acid-free, and washed with water until neutral. Finally, the distillative removal of the solvent and of residues of water is necessary. The overall yield over both stages is said to be 74%-77%. Disadvantages of this process are the large number of work-up operations required, the multiple use of solvents, and the merely moderate yield.

The publication "Diphosphate Ester Plasticizers" in Indust. Eng. Chem. 1950, Volume 42, p. 488, describes a similar process to U.S. Pat. No. 2,782,128, and cites disadvantages of this process as being that the yield, at only 50%, is very low and that there are considerable difficulties in connection with the purification of the intermediates and of the end product. An alternative described is a better process, in which a diol is reacted in a first stage with phosphorus oxychloride to form a tetrachlorobisphosphate, which then, in the second stage, reacts with the alcohol to form the end product. Though the yields are said to be satisfactory, they are not in fact quoted. To work up the reaction mixture from the second stage, pyridine is added, the precipitated pyridine hydrochloride is filtered off with suction, and the product phase is then washed with water. Lastly, pyridine residues have to be removed under reduced pressure.

A disadvantage of this procedure to start with is the difficulty in removing the pyridine residues fully from the end product. Removing the pyridine hydrochloride satisfactorily from the tetraalkyl bisphosphate by filtration is achieved only when its solubility in tetraalkyl bisphosphate is low. A further disadvantage arises from the fact that the product phase is washed with water. If the tetraalkyl bisphosphate is partly miscible with water, then losses of yield in the course of this operation are unavoidable. In the case of tetraalkyl bisphosphates which are miscible with water in any proportion, this washing fails completely, since it is impossible to separate the product from the waste water by phase separation.

U.S. Pat. No. 4,056,480 proposes a similar process for preparing tetraalkyl bisphosphates, in which, again, a diol is reacted in the first stage with phosphorous oxychloride to form a tetrachlorobisphosphate, which in the second stage reacts with the alcohol to form the end product. In the isolation of the end product, instead of pyridine, a dilute sodium hydroxide solution is used. A mixture is formed from which the liquid product phase can be isolated by phase separation. When the excess alcohol has been removed from the product phase by distillation, the product must be washed once again with water and finally freed from residues of water under reduced pressure. The yields of tetraalkyl bisphosphates are 12%-74%.

Disadvantages of this process are, again, the merely moderate yield and the fact that the process involves a number of liquid-liquid phase separations. Consequently, the process is poorly suited to the preparation of partly water-soluble tetraalkyl bisphosphates, and entirely unsuited to the preparation of fully water-soluble tetraalkyl bisphosphates.

It is an object of the present invention to provide a process for preparing fully or partly water-soluble tetraalkyl bisphosphates that is easier to carry out and affords better yields than in the prior art.

Surprisingly it has been found that fully or partly water-soluble tetraalkyl bisphosphates can be prepared easily and in good yield if the hydrogen chloride formed in the reaction of tetrachlorobisphosphates with alcohols is neutralized with a base and the desired product is isolated from the aqueous reaction mixture by extraction. The stated object is thus achieved by means of a process for preparing fully or partly water-soluble tetraalkyl bisphosphates, characterized in that a) a tetrachlorobisphosphate is reacted with one or more alcohols, b) when in step a) at least 50% of the P—Cl groups present in the tetrachlorobisphosphate have reacted, the reaction mixture from step a) is reacted with a base comprising one or more substances of the formula $(Cat^{n+})_a(X^{m-})_b$, in which $Cat^{n+}$ is a cation with a charge of n, $X^{m-}$ is an anion with a charge of m, and a and b are integers which satisfy the condition $n \times a = m \times b$, c) water is added to the reaction mixture from step b), d) thereafter a solvent which is different from the alcohol or alcohols used in step a) and is not fully miscible with water is added to the reaction mixture from step c), to form a mixture consisting of two separate, liquid phases, and e) the phase comprising the tetraalkyl bisphosphate is isolated from the mixture obtained in step d).

Preferably in formula $(Cat^{n+})_a(X^{m-})_b$ n represents 1, 2 or 3 m represents 1, 2 or 3 a represents 1, 2 or 3 and b represents 1, 2 or 3

In one preferred embodiment, the base to be used in step b) consists of one or more substances of the formula $(Cat^{n+})_a(X^{m-})_b$. The term "tetraalkyl bisphosphates" identifies organic substances which contain per molecule two phosphoric ester groups —O—P(=O)(OR)$_2$, where R stands generally for alkyl radicals, and the alkyl radicals R present in a molecule may be identical or different. The term "fully or partly water-soluble" in connection with the present invention identifies substances whose solubility in water at 25° C. is greater than about 1 per cent by weight. The term "tetrachlorobisphosphates" identifies organic substances which contain per molecule two phosphoric ester dichloride groups —O—P(=O)Cl$_2$.

The tetrachlorobisphosphates used in the process of the invention can be prepared by known methods, as are described, for example, in Indust. Eng. Chem. 1950, Volume 42, p. 488 or in U.S. Pat. No. 4,056,480.

The tetrachlorobisphosphates used in the process of the invention correspond preferably to the general formula (I)

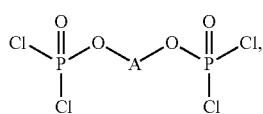
(I)

in which
- A is a straight-chain, branched and/or cyclic C$_4$ to C$_{20}$ alkylene radical, a moiety —CH$_2$—CH=CH—CH$_2$—, a moiety —CH$_2$—C≡C—CH$_2$—, a moiety —CHR$^5$—CHR$^6$—(O—CHR$^7$—CHR$^8$)$_a$—, in which a is a number from 1 to 5, a moiety —CHR$^5$—CHR$^6$—S(O)$_b$—CHR$^7$—CHR$^8$—, in which b is a number from 0 to 2, or a moiety —(CHR$^5$—CHR$^6$)$_c$—O—R$^9$—O—(CHR$^7$—CHR$^8$)$_d$—, in which c and d independently of one another are numbers from 1 to 5,
- R$^5$, R$^6$, R$^7$, R$^8$ independently of one another are H or methyl,
- R$^9$ is a moiety —CH$_2$—CH=CH—CH$_2$—, a moiety —CH$_2$—C≡C—CH$_2$—, a 1,2-phenylene radical, a 1,3-phenylene radical, a 1,4-phenylene radical, a radical of the general formula (II),

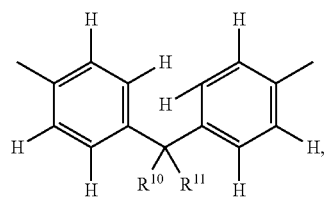
(II)

a radical of the general formula (III),

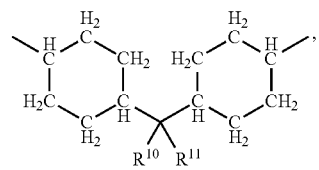
(III)

a radical of the general formula (IV),

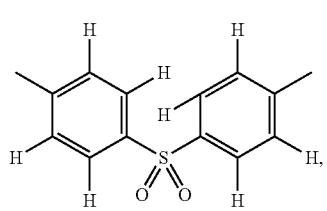
(IV)

or a radical of the formula —C(=O)—R$^{12}$—C(=O)—,
- R$^{10}$ and R$^{11}$ independently of one another are H or C$_1$ to C$_4$ alkyl, or R$^{10}$ and R$^{11}$ together form an optionally alkyl-substituted ring having 4 to 8 C atoms, and
- R$^{12}$ is a straight-chain, branched and/or cyclic C$_2$ to C$_8$ alkylene radical, a 1,2-phenylene radical, a 1,3-phenylene radical, or a 1,4-phenylene radical.

Preferably A is a straight-chain C$_4$ to C$_6$ alkylene radical or preferably A is a moiety of the general formula (III) in which R$^{10}$ and R$^{11}$ are identical and are methyl, a moiety of the formula (V), (VI) or (VII),

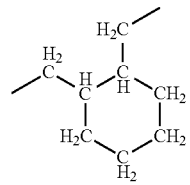
(V)

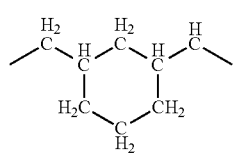
(VI)

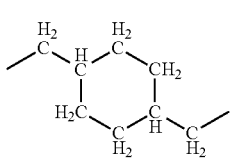
(VII)

or preferably A is a moiety —CHR$^5$—CHR$^6$—(O—CHR$^7$—CHR$^8$)$_a$—, in which a is a number from 1 to 2 and R$^5$, R$^6$, R$^7$ and R$^8$ are identical and are H or preferably A is a moiety —(CHR$^5$—CHR$^6$)$_c$—O—R$^9$—O—(CHR$^7$—CHR$^8$)$_d$—, in which c and d independently of one another are a number from 1 to 2, R$^9$ is a moiety of the general formula (II) and R$^{10}$ and R$^{11}$ are identical and are methyl.

With particular preference A is a radical selected from the group consisting of —CH$_2$CH$_2$—O—CH$_2$CH$_2$—, —CH$_2$CH$_2$CH$_2$CH$_2$— and —CH$_2$—CH(CH$_2$CH$_2$)$_2$CH—CH$_2$—.

The alcohols used in the process of the invention are preferably selected from the group consisting of methanol, ethanol, 1-propanol, 2-propanol, 2-methyl-1-propanol, 1-butanol and 2-butanol. It is particularly preferred to use methanol and ethanol.

The bases of the formula $(Cat^{n+})_a(X^{m+})_b$ used in the process of the invention are preferably ammonium salts, alkali metal salts or alkaline earth metal salts. The anion these salts comprise is preferably hydroxide, alkoxide, oxide, carbonate, hydrogencarbonate, phosphate, hydrogenphosphate, dihydrogenphosphate or acetate. Particular preference is given to ammonium hydroxide, lithium hydroxide, sodium hydroxide, sodium methoxide, sodium ethoxide, sodium carbonate, sodium hydrogencarbonate, trisodium phosphate, disodium hydrogenphosphate, sodium acetate, potassium hydroxide, potassium tert-butoxide, potassium carbonate, potassium hydrogencarbonate, caesium hydroxide, magnesium hydroxide, magnesium oxide, calcium hydroxide, calcium methoxide or calcium oxide. Employed with more particular preference are sodium hydroxide, sodium carbonate, sodium hydrogencarbonate, potassium hydroxide, potassium carbonate or potassium hydrogencarbonate.

Step a) of the process of the invention is carried out using at least four mole equivalents of alcohol per mole equivalent of tetrachlorobisphosphate. The reactants can be reacted with one another in bulk or in solution in a solvent. Suitable solvents are toluene, heptane and dichloromethane, and also an excess of the alcohol used in the reaction. The tetrachlorobisphosphate is introduced into a reaction vessel and the alcohol is metered in. Alternatively, the alcohol is introduced into a reaction vessel and the tetrachlorobisphosphate is metered in. It is also possible for alcohol and tetrachlorobisphosphate to be metered in parallel into a reaction vessel. In place of the pure reactants, solutions of the reactants can also be metered.

In the reaction which then proceeds, the P—Cl groups of the tetrachlorobisphosphate are converted, by reaction with the alcohol, into P—OR groups, and hydrogen chloride is liberated.

The reaction is carried out preferably at temperatures between −10° C. and +70° C. and under pressures between 10 and 6000 mbar. The reactants are contacted with one another in this procedure by means of suitable measures, more particularly by stirring.

By-product hydrogen chloride formed in the reaction is preferably left substantially in the reaction mixture and neutralized with the base in step b) of the process. In an alternative, likewise preferred embodiment of the process, the hydrogen chloride formed as a by-product in step a) is removed in circulation at least partly from the reaction vessel. This is done, for example, by application of a vacuum or by the passing of an inert gas such as nitrogen or carbon dioxide through the reaction vessel.

In one alternative embodiment, step a) may involve further, optional separative operations, such as a distillation to remove unreacted alcohol, for example.

The subsequent step b) is carried out only when at least 50% of the P—Cl groups present in the tetrachlorobisphosphate have been reacted in step a). The conversion of the P—Cl groups can be monitored analytically, preferably by means of $^{31}$P-NMR spectroscopy.

For the implementation of step b), the reaction mixture obtained in step a) is contacted with the base, preferably with thorough mixing. The amount of the base is selected such that the reaction mixture after step b) preferably has a pH between 6 and 11. With particular preference the reaction mixture after step b) has a pH between 7 and 10.

The base is preferably introduced in a meterable form into the reaction vessel of step a). Alternatively and likewise preferably, the base in a suitable form is introduced into a second reaction vessel, and the reaction mixture from step a) is transferred to this vessel.

Suitable and preferred meterable forms of the base are, for example, powders, granules, solutions or dispersions. One particularly preferred embodiment of the process uses the base in the form of an aqueous solution or dispersion. Very particular preference is given to using a 10%-60% strength by weight aqueous solution of sodium hydroxide, sodium carbonate, potassium hydroxide and/or potassium carbonate.

An alternative, likewise preferred embodiment of the process uses the base in the form of a powder having an average particle size of 0.1 μm to 2000 μm. Particular preference in this case is given to using powderous sodium carbonate, sodium hydrogencarbonate, potassium carbonate and/or potassium hydrogencarbonate.

Step b) is carried out preferably at temperatures between 5° C. and 70° C. and under pressures between 10 and 6000 mbar.

Step b) may entail further, optional separative operations, preferably a distillation for the removal of unreacted alcohol from step a).

In step c) of the process of the invention, water is added to the reaction mixture obtained in step b), and the resulting mixture is mixed thoroughly in a suitable way. As a result, the salt $CatCl_n$ is converted into an aqueous solution, and all of the solids are substantially dissolved. The addition of water may also be accomplished by the introduction of the water in step b) itself, in the form of an aqueous solution or dispersion.

Step c) is carried out preferably at temperatures between 5° C. and 70° C. and under pressures between 10 and 6000 mbar.

Step c) may entail further, optional separative operations, preferably a filtration for the removal of water-insoluble solids or a distillation for the removal of unreacted alcohol from step a).

In step d) a solvent is added which is different from the alcohol or alcohols used in step a) and is not fully miscible with water. It is also possible to employ a combination of two or more solvents. The solvents are preferably selected from the group consisting of aliphatic hydrocarbons, more particularly pentane, hexane, cyclohexane, heptane, aromatic hydrocarbons, more particularly benzene, toluene, xylene, halohydrocarbons, more particularly methylene chloride, chloroform, dichloroethane, trichloroethylene, tetrachloroethylene, 1-chlorobutane, chlorobenzene, 1,2-dichlorobenzene, alcohols, more particularly 1-butanol, 1-pentanol, 1-hexanol, cyclohexanol, ethers, more particularly diethyl ether, methyl tert-butyl ether, dibutyl ether, ketones, more particularly 2-butanone, 3-pentanone, 4-methyl-2-pentanone, cyclohexanone, or esters, more particularly ethyl acetate, 1-butyl acetate, 1-pentyl acetate.

The precise amounts of water in step c) and of solvent in step d) are not critical for the attainment of a phase separation. The required amounts of water and of solvent can be determined easily by means of simple tests. The amounts of water in step c) and of solvent in step d) are preferably selected such that the volume ratio of aqueous phase to organic phase is between 20:1 and 1:20. With particular preference the amounts are selected such that the volume ratio of aqueous phase to organic phase is between 10:1 and 1:10.

In step e) of the process of the invention, the two phases obtained in step d) are separated, and the phase containing the tetraalkyl bisphosphate is worked up by conventional methods.

For the isolation of the product phase, the conventional methods for separating liquid-liquid mixtures are employed, preferably decanting or centrifuging. The isolated product phase can be subjected preferably to a further phase separation or to a plurality of phase separations and, if necessary, passed on for a subsequent purification, preferably by filtration, clarification, extraction, distillation or drying, or by a suitable combination of these methods.

Steps b), c) and d) of the process of the invention are carried out in any order in succession or fully or partly simultaneously.

Preferably, steps d) and e) are carried out repeatedly in succession.

The process of the invention is used preferably for preparing fully water-soluble tetraalkyl bisphosphates.

Any one of the four steps of the process can be carried out discontinuously or continuously. The overall process may consist of any desired combinations of steps carried out continuously or discontinuously.

The process of the invention allows the synthesis of fully or partly water-soluble tetraalkyl bisphosphates in a better yield than by the known processes and in a high purity.

The examples below are used to elucidate the invention in more detail, without any intention that they should restrict the invention. The parts referred to are by weight. For clarification it is noted that the scope of the present invention encompasses all parameters and definitions set out above, given generally or stated in ranges of preference, and in any desired combinations.

EXAMPLES

Example 1

Preparation of diethylene glycol bis(dichlorophosphate) (Not Inventive)

A 1000 ml four-necked flask with stirrer, thermometer, dropping funnel with pressure compensation and reflux condenser was charged with 984.3 g of phosphoryl chloride at 20° C. Then a vacuum of approximately 670 mbar was applied and 332.3 g of diethylene glycol were added dropwise over the course of 4 hours. Cooling in an ice-water bath kept the temperature at 20° C. A clear, colourless reaction mixture was formed. After the end of the metered addition, the pressure was lowered to about 6 mbar, and stirring was continued at 25° C. for 16 hours. This left 1055.7 g (98%) of diethylene glycol bis(dichlorophosphate).

Example 2

Preparation of tetraethyldiethylene glycol bisphosphate (Inventive)

A 1000 ml four-necked flask with stirrer, thermometer, dropping funnel with pressure compensation and reflux condenser was charged under a nitrogen atmosphere with 169.8 g of diethylene glycol bis(dichlorophosphate) from Example 1, and this initial charge was cooled to 10° C. At this temperature, 350 ml of ethanol were added dropwise over the course of 50 minutes. Dry ice pellets were dropped in to keep the temperature at 10-15° C. The colourless solution was subsequently stirred at 15° C. for 1 hour and then at 23° C. for 2 hours. The colourless and clear synthesis solution was then admixed dropwise over the course of 2 hours with a mixture of 340 ml of water and 155 g of 50% strength sodium hydroxide solution. Cooling in an ice-water bath kept the temperature at 20° C. The mixture was subsequently stirred at 23° C. for 16 hours and then extracted with four times 100 ml of dichloromethane. The combined extract solutions were concentrated under reduced pressure on a rotary evaporator. Lastly, the product was filtered off on a Büchner funnel.

| Yield | 172.2 g (91%) colourless liquid |
|---|---|
| Acid number | <0.1 mg KOH/g |
| Sodium content | 1178 ppm |

Example 3

Preparation of tetraethyldiethylene glycol bisphosphate (Inventive)

A 1000 ml four-necked flask was charged under $N_2$ with 169.8 g of diethylene glycol bis(dichlorophosphate) from Example 1 at 5° C. At this temperature, over the course of 50 minutes, 276.4 g of ethanol were added dropwise. The reaction mixture showed an exothermic reaction. An ice-water bath was used to keep the temperature of the reaction mixture at 10° C. The clear, slightly orange-brownish solution was subsequently stirred at 10° C. for 2 hours, then warmed to 20° C. and stirred for a further 18 hours. A 2 l glass beaker was charged with 340 ml of fully demineralized water, and 155 g of 50% strength sodium hydroxide solution were added with stirring. The mixture was cooled to 23° C. The above synthesis solution was then metered in over the course of 2 hours, accompanied by formation of a slight mist. The temperature was held at 23° C. by means of external cooling. The yellowish mixture, which at the end was still acidic, was clear and single-phase. It was adjusted to a pH of 7.5 using a little 20% strength aqueous sodium carbonate solution, and then extracted by shaking with four times 100 ml of methylene chloride. The slightly yellowish, turbid organic phases were combined and concentrated under reduced pressure on a rotary evaporator. In order to clarify the product, it was, lastly, also filtered off with suction on a round paper filter.

| Yield | 159.3 g (84%) yellowish liquid |
|---|---|
| Acid number | <0.1 mg KOH/g |
| Sodium content | 1794 ppm |

Example 4

Preparation of tetraethyldiethylene glycol bisphosphate (Inventive)

A 1000 ml four-necked flask with stirrer, thermometer, dropping funnel with pressure compensation and reflux condenser was charged under a nitrogen atmosphere with 169.8 g of diethylene glycol bis(dichlorophosphate) from Example 1, and this initial charge was cooled to 10° C. At this temperature, 350 ml of ethanol were added dropwise over the course of 50 minutes. Dry ice pellets were dropped in to keep the temperature at 10-15° C. The colourless solution was subsequently stirred at 15° C. for 1 hour and then at 20° C. for 2 hours. The synthesis solution was then admixed dropwise over the course of 2 hours with a mixture of 340 ml of water and 155 g of 50% strength sodium hydroxide solution. Cooling in an ice-water bath kept the temperature at 20° C. The mixture was subsequently stirred at 23° C. for 16 hours and then extracted with four times 100 ml of toluene. The combined extract solutions were concentrated under reduced pressure on a rotary evaporator. Lastly, the product was filtered off with suction on round paper filters.

| Yield | 169.2 g (89%) colourless liquid |
|---|---|
| Acid number | <0.1 mg KOH/g |
| Sodium content | 1546 ppm |

Example 5

Preparation of tetraethyldiethylene glycol bisphosphate (Inventive)

A 1000 ml four-necked flask with stirrer, thermometer, dropping funnel with pressure compensation and reflux condenser was charged under a nitrogen atmosphere with 350 ml of ethanol and this initial charge was cooled to 15° C. At this temperature, over the course of 35 minutes, 169.8 g of diethylene glycol bis(dichlorophosphate) from Example 1 were added dropwise. External cooling maintained the temperature at 15-20° C. The colourless solution was subsequently stirred at 20° C. for 4 hours. The colourless and clear synthesis solution was then cooled to 15° C. and adjusted to a pH of 2 by addition of 192.1 g of 50% strength sodium hydroxide solution over the course of 40 minutes. During this time, cooling in an ice-water bath kept the temperature at 20-25° C. The a few ml of 10% strength sodium hydroxide solution were added, setting the pH to 8.5. The mixture obtained was stirred at 23° C. for 16 hours and then concentrated under reduced pressure on a rotary evaporator at 20 mbar and 50° C. The residue obtained was admixed with 400 ml of water, stirred for 30 minutes, and then extracted with three times 100 ml of dichloromethane. The combined extract solutions were concentrated under reduced pressure on a rotary evaporator. The residue which remained in this concentration process was filtered.

| Yield | 172.9 g (91%) colourless liquid |
|---|---|
| Acid number | <0.1 mg KOH/g |
| Sodium content | 530 ppm |

Example 6

Preparation of tetramethyldiethylene glycol bisphosphate (Inventive)

The process indicated in Example 2 was used to prepare tetramethyldiethylene glycol bisphosphate from 250 ml of methanol and 169.8 g of diethylene glycol bis(dichlorophosphate) from Example 1.

| Yield | 145.1 g (90%) colourless liquid |
|---|---|
| Acid number | <0.1 mg KOH/g |
| Sodium content | 1254 ppm |

Example 7

Preparation of tetra-n-butyldiethylene glycol bisphosphate (Inventive)

The process indicated in Example 2 was used to prepare tetra-n-butyldiethylene glycol bisphosphate from 600 ml of n-butanol and 169.8 g of diethylene glycol bis(dichlorophosphate) from Example 1.

| Yield | 217.8 g (89%) colourless liquid |
|---|---|
| Acid number | <0.1 mg KOH/g |
| Sodium content | 1935 ppm |

Example 8

Preparation of 1,4-butanediol bis(dichlorophosphate) (Not Inventive)

A 500 ml four-necked flask with stirrer, thermometer, dropping funnel with pressure compensation and reflux condenser was charged with 300.0 g of phosphoryl chloride at 20° C. Then a vacuum of 200 mbar was applied and 45.0 g of 1,4-butanediol were added dropwise over the course of 45 minutes. Cooling in an ice-water bath kept the temperature at 20° C. A clear, colourless reaction mixture was formed. After the end of the metered addition, the pressure was lowered to about 100 mbar, and stirring was continued for 2 hours. A distillation bridge was then mounted on, and the excess of phosphoryl chloride was removed by distillation. This left 144.9 g (91%) of 1,4-butanediol bis(dichlorophosphate).

Example 9

Preparation of tetraethyl-1,4-butanediol bisphosphate (Inventive)

The process indicated in Example 2 was used to prepare tetraethyl-1,4-butanediol bisphosphate from 350 ml of ethanol and 161.8 g of 1,4-butanediol bis(dichlorophosphate) from Example 7.

| Yield | 160.2 g (88%) colourless liquid |
|---|---|
| Acid number | 0.13 mg KOH/g |
| Sodium content | 1085 ppm |

Example 10

Solubility of tetraalkyl bisphosphates in Water (Inventive)

A separating funnel was charged with 50.0 g of tetraalkyl bisphosphate and 50.0 g of fully demineralized water, and was shaken vigorously and then left to stand at an ambient temperature of 25° C. for 1 hour. If phase separation became apparent, the lower, aqueous phase was carefully separated off and weighed ($m_W$). The aqueous phase was concentrated to constant weight under reduced pressure on a rotary evaporator, and the residue was likewise weighed ($m_R$). The variable $m_R/m_W \times 100\%$ was calculated, as a measure of the solubility in water, and has been listed in Table 1.

With the substances tetramethyldiethylene glycol bisphosphate and tetraethyldiethylene glycol bisphosphate, there was no phase separation in the experiment described above. Further experiments with different weight ratios of tetraalkyl bisphosphate and water likewise gave no phase separation for these substances. This means that tetramethyldiethylene glycol bisphosphate and tetraethyldiethylene glycol bisphosphate are fully water-soluble.

TABLE 1

Solubility of tetraalkyl bisphosphates in water

| Tetraalkyl bisphosphate | $m_R/m_W \times 100\%$ |
|---|---|
| Tetraethyldiethylene glycol bisphosphate (Examples 2-5) | no phase separation |
| Tetramethyldiethylene glycol bisphosphate (Example 6) | no phase separation |

TABLE 1-continued

Solubility of tetraalkyl bisphosphates in water

| Tetraalkyl bisphosphate | $m_R/m_W \times 100\%$ |
|---|---|
| Tetra-n-butyldiethylene glycol bisphosphate (Example 7) | 3% |
| Tetraethyl-1,4-butanediol bisphosphate (Example 9) | 26% |

EVALUATION

Example 10 shows that the tetraalkyl bisphosphates under consideration are fully or partly miscible with water. These substances, therefore, according to the preparation processes from the prior art, can be prepared only in a poor yield or not at all. Examples 2 to 7 and 9 show that tetraalkyl bisphosphates can be prepared easily and in high yield by the process of the invention. Products of high purity are obtained in this case, as can be gleaned from the low acid numbers and sodium contents. It is surprising that preparation is possible successfully in particular in the case of partly or fully water-soluble tetraalkyl bisphosphates.

Fully demineralized water in the sense of the present invention is characterized by possessing a conductivity of 0.1 to 10 μs, with the amount of dissolved or undissolved metal ions being not greater than 1 ppm, preferably not greater than 0.5 ppm for Fe, Co, Ni, Mo, Cr and Cu as individual components, and not greater than 10 ppm, preferably not greater than 1 ppm, for the stated metals in total.

What is claimed is:

1. A process for preparing a fully or partly water-soluble tetraalkyl bisphosphate, in which
   a) a bis(dichlorophosphate) is reacted with one or more alcohols,
   b) when in step a) at least 50% of the P—Cl groups present in the bis(dichlorophosphate) have reacted, the reaction mixture from step a) is reacted with a base comprising one or more substances of the formula $(Cat^{n+})_a(X^{m-})_b$, in which $Cat^{n+}$ is a cation with a charge of n, $X^{m-}$ is an anion with a charge of m, and a and b are integers which satisfy the condition $n \times a = m \times b$,
   c) water is added to the reaction mixture from step b),
   d) thereafter a solvent which is different from the alcohol or alcohols used in step a) and which is not fully miscible with water is added to the reaction mixture from step c), to form a mixture consisting of two separate, liquid phases, and
   e) the phase comprising the tetraalkyl bisphosphate is isolated from the mixture obtained in step d).

2. The process of claim 1, in which the bis(dichlorophosphate) is a substance of the formula (I)

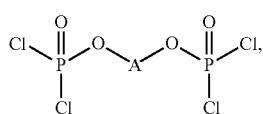
(I)

in which
A is a straight-chain, branched and/or cyclic $C_4$ to $C_{20}$ alkylene radical, a moiety —$CH_2$—CH=CH—$CH_2$—, a moiety —$CH_2$—C≡C—$CH_2$—, a moiety —$CHR^5$—$CHR^6$—(O—$CHR^7$—$CHR^8$)$_a$— in which a is a number from 1 to 5, a moiety —$CHR^5$—$CHR^6$—S(O)$_b$—$CHR^7$—$CHR^8$— in which b is a number from 0 to 2, or a moiety —($CHR^5$—$CHR^6$)$_c$—O—$R^9$—O—($CHR^7$—$CHR^6$)$_d$— in which c and d independently of one another are numbers from 1 to 5, $R^5$, $R^6$, $R^7$, $R^8$ independently of one another are H or methyl, $R^9$ is a moiety —$CH_2$—CH=CH—$CH_2$—, a moiety —$CH_2$—C≡C—$CH_2$—, a 1,2-phenylene radical, a 1,3-phenylene radical, a 1,4-phenylene radical, a radical of the formula (II),

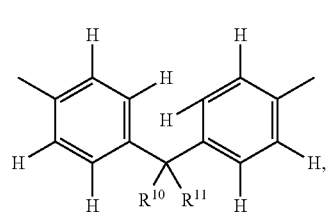
(II)

a radical of the formula (III),

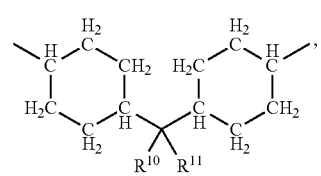
(III)

a radical of the formula (IV),

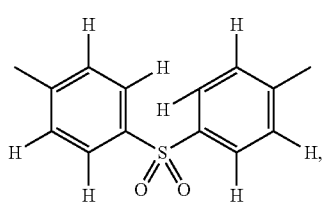
(IV)

or a radical of the formula —C(=O)—$R^{12}$—C(=O)—, $R^{10}$ and $R^{11}$ independently of one another are H or $C_1$ to $C_4$ alkyl, or $R^{10}$ and $R^{11}$ together form an alkyl-substituted or unsubstituted ring having 4 to 8 C atoms, and $R^{12}$ is a straight-chain, branched and/or cyclic $C_2$ to $C_8$ alkylene radical, a 1,2-phenylene radical, a 1,3-phenylene radical, or a 1,4-phenylene radical.

3. The process of claim 2, in which that A is a straight-chain $C_4$ to $C_6$ alkylene radical, a moiety of the formula (III) in which $R^{10}$ and $R^{11}$ are identical and are methyl, or is a moiety of the formulae (V), (VI) or (VII),

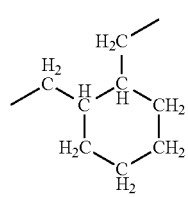
(V)

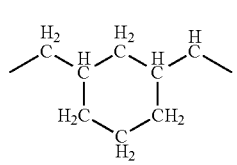
(VI)

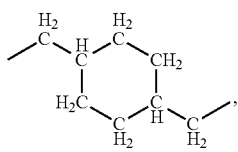
(VII)

or is a moiety —CHR⁵—CHR⁶—(O—CHR⁷—CHR⁸)$_a$—, or a moiety —(CHR⁵—CHR⁶)$_c$—O—R⁹—O—(CHR⁷—CHR⁸)$_d$— in which c and d independently of one another are a number from 1 to 2, $R^5$, $R^6$, $R^7$, and $R^8$ are identical and are H and $R^9$ is a moiety of the formula (II) in which $R^{10}$ and $R^{11}$ are identical and are methyl.

4. The process of claim 2, in which A is a radical selected from the group consisting of —CH₂CH₂—O—CH₂CH₂—, —CH₂CH₂CH₂CH₂— and —CH₂—CH(CH₂CH₂)₂CH—CH₂—.

5. The process of claim 1, in which the alcohol is selected from the group consisting of methanol, ethanol, 1-propanol, 2-propanol, 2-methyl-1-propanol, 1-butanol and 2-butanol.

6. The process of claim 1, in which the alcohol is selected from the group consisting of methanol and ethanol.

7. The process of claim 1, in which $Cat^{n+}$ is a substituted or unsubstituted ammonium ion, an alkali metal on or an alkaline earth metal on and $X^{m-}$ is a hydroxide, an alkoxide, an oxide, a carbonate, a hydrogencarbonate, a phosphate, a hydrogenphosphate, a dihydrogenphosphate or an acetate.

8. The process of claim 1, in which the amount of the base is selected such that the reaction mixture after step b) has a pH between 6 and 11.

9. The process of claim 1, in which the base is used in the form of an aqueous solution or dispersion.

10. The process of claim 9, wherein the base is a 10%-60% strength by weight aqueous solution of sodium hydroxide, sodium carbonate, potassium hydroxide or potassium carbonate or a mixture thereof.

11. The process of claim 1, in which the base is powder having an average particle size of 0.1 μm to 2000 μm.

12. The process of claim 11, wherein the base is a powderous sodium carbonate, sodium hydrogencarbonate, potassium carbonate or potassium hydrogencarbonate or a mixture thereof.

13. The process of claim 1, characterized in which one or more solvents are used from the group consisting of aliphatic hydrocarbons, aromatic hacrocarbons, halohydrocarbons, alcohols, ethers, ketones and esters.

14. The process of claim 1, in which steps b), c) and d) are carried out in succession in any order.

15. The process of claim 1 in which steps b), c) and d) are carried out fully or partly simultaneously.

16. The process of claim 1 in which steps d) and e) are carried out repeatedly in succession.

17. The process of claim 1, characterized in which one or more of steps a) to e) are carried out discontinuously.

18. The process of claim 1, in which one or more of step a) to e) are carried out continuously.

19. The process of claim 1, in which the tetraalkyl bisphosphate is fully water-soluble.

\* \* \* \* \*